United States Patent [19]

Scheurer et al.

[11] Patent Number: 4,882,161

[45] Date of Patent: Nov. 21, 1989

[54] CHEWABLE, NON-GRITTY CALCIUM CITRATE TABLET

[75] Inventors: Heinrich P. Scheurer; Adrian G. McNamee, both of Scarborough, Canada

[73] Assignee: Warner-Lambert Company, Morris Plains, N.J.

[21] Appl. No.: 140,014

[22] Filed: Dec. 31, 1987

[51] Int. Cl.<sup>4</sup> .................................................. A61K 9/28
[52] U.S. Cl. .................................... 424/441; 424/469; 424/493
[58] Field of Search ........................ 424/439, 440, 441

[56] References Cited

U.S. PATENT DOCUMENTS 4,543,254   9/1985   Kaneko et al. ...................... 514/253

Primary Examiner—Thurman K. Page
Assistant Examiner—Leon L. Horne
Attorney, Agent, or Firm—Daniel A. Scola, Jr.

[57] ABSTRACT

A non-gritty chewable calcium tablet comprising a granulation having a bulk density of about 0.3 g/ml to about 1.5 g/ml, said granulation comprising micronized calcium citrate, a sweetener and a lubricant. The calcium particle size is in the range of about 0.1 micronmeters to about 10 micronmeters.

15 Claims, No Drawings

CHEWABLE, NON-GRITTY CALCIUM CITRATE TABLET

This invention concerns a non-gritty, chewable calcium tablet which has improved palatability and calcium bioavailability due to the use of a granulation of micronized citrate, sweetener and lubricant. More specifically, the granulation has a specified bulk density and micronized calcium citrate particle size range which are critical to the formation of a non-gritty chewable tablet having readily available calcium.

The use of calcium citrate is well known as a source of calcium in nutrient supplements and the like. Calcium citrate is disclosed in the literature as actually being more readily bioavailable than other more commonly used calcium salts such as calcium carbonate and calcium phosphate. Calcium has been recognized recently as a potential means of minimizing osteoporotic development, particularly in post menopausal women and aging people of both sexes. Additionally, the citrate form is reported as raising urinary citrate, which may retard the formation of calcium kidney stones, a concern for those ingesting large amounts of calcium on a regular basis.

The disadvantage of forming a chewable tablet with calcium salts is the objectionable grittiness and mouth feel which result in an unpalatable and commercially unacceptable product. Since the intake of calcium is particularly important to certain classes of people, such as postmenopausal women and the elderly, it is critical that a product be available which encourages a high compliance to the prescribed daily regimen to insure adequate intake. Tablets are commercially available using calcium carbonate as the calcium source, but as previously discussed, calcium in this form is not believed to be as bioavailable as calcium citrate. Calcium citrate, on the other hand, is commercially available only in its crystalline form in a size range of about 60 to 100 mesh (U.S. standard), equivalent to about 250 to 150 micrometers. Compressed tablets formed from calcium citrate in these particle ranges result in tablets which are extremely gritty and unpalatable. Such tablets would not be considered commercially acceptable to patients for whom compliance may be a concern.

The instant invention solves the above disadvantages of the prior art by providing a granulation designed to overcome the inherent grittiness of calcium citrate. More particularly, the instant invention comprises a non-gritty, chewable calcium tablet comprising a granulation having a bulk density of about 0.3/ml to about 1.5 g/ml, said granulation comprising micronized calcium citrate having a particle size from about 0.1 micronmeters to about 10.0 micronmeters, a sweetener and a lubricant. This invention additionally provides for the granulation per se. which may be incorporated into other dosage forms such as capsules or sold directly in its free-flowing granulated form. Since micronized calcium citrate is not commercially available within the required particle size, it was necessary to perform the micronization after purchase in order to make the instant invention.

More particularly the instant invention concerns a non-gritty, chewable calcium tablet comprising a granulation having a bulk density of about 0.3 g/ml to about 1.5 g/ml, said granulation comprising micronized calcium citrate having a particle size from about 0.1 micronmeters to about 10.0 micronmeters, a sweetener and a lubricant. The tablet is made with a hardness range of about 5 to about 20 Strong Cobb Units (SCU) such that it retains its structural integrity during handling and packaging but is soft enough to easily chew and dissolve in the mouth. Each SCU is equivalent to about 0.71 kilogram per square inch (Kg/in2). The bulk density of the granulation within the ranges disclosed above are best suited for producing the inventive tablets and allows for a soft, chewable tablet which tastes smooth. Preferably the bulk density is about 0.5 to about 1.0 g/ml. It has been determined that the bulk density must be kept within the above-mentioned ranges to remain fluffy and retain its smooth taste. Of course, these ranges of calcium citrate particle size and final granulation bulk density must be balanced properly to produce a smooth, non-gritty granulation. The finer the size, the more difficult it is to form a granulation.

The particle size of the calcium citrate is indeed critical to the non-gritty character of the invention. Presently, the commercially available calcium citrate is available only at particle sizes in the range of about 150 to about 250 microns, and calcium tablets manufactured from such material, even after milling to about the 1 to 30 micron size are unacceptably gritty and exhibit an unpleasant mouth feel. It has been discovered, however, that when calcium citrate is micronized into a particle size range of about 0.1 to about 10 micronmeters, non-gritty chewable tablets can be produced. The particle range is indeed critical to this result and tablets made outside this range exhibit significant mouthfeel disadvantages as compared to the inventive product. Preferably the particle size of the calcium citrate is about 0.1 to about 5 and most preferably about 0.1 to about 3 micronmeters. Calcium citrate is the salt of choice because of its greater bioavailability than other calcium salts. Calcium citrate comprises from about 25 to about 90% by weight of the total tablet composition. Calcium citrate is not readily soluble in water and thus does not dissolve easily in the mouth. Thus, the commercially available particle size is readily perceptible as being gritty as well as chalky during chew. The commercial grade of this salt is crystalline and does not yield a pleasant mouthfeel. Once ingested, the salt easily dissolves in the stomach. Another alternative to hard, chewable tablets is capsules. Capsules containing calcium citrate are not as fast to dissolve as the micronized calcium citrate, in the chewable dosage form of the instant invention. The combination of fine, micronized calcium citrate particle size and mastication of the tablet initiates a more rapid dissolution of the calcium and facilitates absorption once fully ingested.

In addition to the requirement of a specific calcium citrate particle size, the granulation contains a sweetener and a lubricant. The sweetener may be selected from any number of the natural or artificial sweeteners commonly used. For example, a non-limiting list includes: sucrose, glucose, mannose, galactose, saccharin and its salts, cyclamates, acesulfame salts, talin, monellin, dihydrochalcone, dipeptides, polyols, amino-acid based sweeteners such as aspartame, chlorinated sucrose derivatives (sucralose), as well as numerous others. Mixtures of these sweeteners are also useful. Bulk sweeteners such as sugar and polyols are present in the instant invention in amounts of about 10 to about 60% by weight. High intensity sweeteners are generally used in the range of about 0.1 to about 2% by weight.

The lubricant is the third and final component of the granulation and is preferably chosen from the class of metal stearates such as sodium, calcium, potassium and magnesium stearates. Magnesium stearate is the preferred lubricant. Other useful lubricants include talc, sodium lauryl sulfate, polyethylene glycols and other commonly known tableting lubricants such as natural waxes, synthetic waxes and petroleum waxes (e.g. paraffin wax). Additionally such components as sodium acetate, sodium benzoate and sodium oleate are useful lubricants. The lubricants are generally processing aids which facilitate tablet compression and prevent sticking of the material to punches and other tablet forming equipment. Lubricants may be present in amounts of about 0.1 to about 5% and preferably about 0.5 to about 2% by weight.

Additionally ingredients such as water (for granulating), coloring agents, flavoring agents excipients, diluents, binders, bulking agents and the like may be employed for their commonly known intended purposes. These ingredients may be present in amounts of about 0.1 to about 25% by weight. These ingredients may be used to achieve specific adjustments to the formulations for taste purposes as well as to achieve specific results in the final product. The final moisture content of the instant compositions is generally about 0.5 to about 1.5% by weight.

Examples of flavors useful include synthetic flavoring liquids and/or liquids derived from plants, leaves, flowers, fruits and so forth, as well as combinations thereof. Representative flavoring liquids include: plant oils such as spearmint oil, peppermint oil, oil of wintergreen (methylsalicylate) and cinnamon oil; natural or synthetic fruit flavors such as citrus oil including lemon, orange, grape, lime pineapple and grapefruit; and fruit essences including apple, strawberry, cherry, banana and so forth.

The amount of flavoring agent employed is normally a matter of preference subject to such factors as flavor type and strength desired. In general, amounts of about 0.05 to about 2% by weight are useful.

Lactose, microcrystalline cellulose and starches derived from wheat, corn rice and potato in finely divided powders are useful as bulking agents or diluents. Natural gums, alginates, silicates and polymers such as polyvinylpyrrolidone, and ethyl and methylcellulose maybe used as binders.

Micronized calcium citrate itself will not compress to form a structural tablet. Thus, tablets of the instant invention are formed from a granulation using conventional wet granulation techniques. To prepare such a granulation, powdered, micronized calcium citrate (within the prescribed particle ranges), sweetener (e.g. milled sugar, saccharin) and flavor (citric acid) are blended in a Glatt granulator. Once these ingredients are fully integrated to form a homogenous blend, an aqueous solution (15°–75°) of sweetener (e.g., sugar), or plain water (15°–75° C.) is sprayed on the mixture to form wet granules. The granules are then dried and sized prior to adding a lubricant (e.g, magnesium stearate). Additional ingredients such as volatile flavoring agents may be incorporated at this time. The sized particles are then compressed on tablet-making machinery and packaged.

The following examples serve to provide further appreciation of the invention but are not meant in any way to restrict the effective scope of the invention. All percentages throughout the specification are by weight % of the final delivery system unless otherwise indicated.

TABLE I

| NON-MICRONIZED CALICUM CITRATE (COMMERCIALLY AVAILABLE CRYSTALLINE FORM)* | | | | | | |
|---|---|---|---|---|---|---|
| | 1 | 2 | 3 | 4 | 5 | 6 |
| Calcium Citrate Tetrahydrate (milled) (Non-micronized) | 71.2% | 71.2% | 71.2% | 71.2% | 71.2% | 7.12% |
| Sugar (6X) | 18.1% | 18.1% | 18.1% | 16.8% | 11.9% | 11.9% |
| Sugar (Fine) | 10.0% | 10.0% | 10.0% | 10.0% | 15.0% | 15.0% |
| Cyclamate | — | — | 0.5% | 0.7% | — | 0.6% |
| Citric Acid | — | — | — | 0.5% | 0.5% | 0.5% |
| Saccharin | — | — | — | — | 0.15% | — |
| Polyol Crystals | — | — | — | — | — | — |
| Sorbitol Solution (70%) | — | — | — | — | — | — |
| Flavor | 0.2% | 0.4% | 0.4% | 0.3% | 0.7% | 0.17% |
| Magnesium Stearate | 0.5% | 0.5% | 0.5% | 0.5% | 0.5% | 0.5% |
| **Water (Potable) | 35% | 35% | 35% | 35% | 25% | 24% |
| Tablet Weight | 2.0 g | 2.0 g | 2.0 g | 2.0 g | 2.0 g | 2.0 g |
| Tablet Harness (SCU) | 14–18 SCU | 10–14 SCU | 13–15 SCU | 15–17 SCU | 14–16 SCU | 15–17 SCU |
| Milligrams of Calcium | 300 mg | 300 mg | 300 mg | 300 mg | 300 mg | 300 mg |
| | 7 | 8 | 9 | 10 | 11 | 12 |
| Calcium Citrate Tetrahydrate (milled) (Non-micronized) | 79.3% | 79.3% | 79.3% | 71.2% | 71.2% | 71.2% |
| Sugar (6X) | 3.93% | 4.48% | 4.48% | 13.1% | 12.6% | 12.6% |
| Sugar (Fine) | 15.0% | 15.0% | 15.0% | 15.0% | 15.0% | 15.0% |
| Cyclamate | 0.7% | — | — | — | — | — |
| Citric Acid | 0.5% | 0.5% | 0.5% | 0.5% | 0.5% | 0.5% |
| Saccharin | — | 0.15% | 0.15% | 0.1% | 0.1% | 0.1% |
| Polyol Crystals | — | — | — | — | — | — |
| Sorbitol Solution (70%) | — | — | — | — | — | — |

TABLE I-continued

NON-MICRONIZED CALICUM CITRATE
(COMMERCIALLY AVAILABLE CRYSTALLINE FORM)*

| | | | | | | |
|---|---|---|---|---|---|---|
| Flavor | 0.17% | 0.1% | 0.17% | 0.10% | 0.12% | 0.18% |
| Magnesium Stearate | 0.5% | 0.5% | 0.5% | 0.5% | 0.5% | 0.5% |
| **Water (Potable) | 37% | 40% | 40% | 28% | 28% | 28% |
| Tablet Weight | 2.0 g | 2.0 g | 2.0 g | 1.667 g | 2.0 g | 2.0 g |
| Tablet Harness (SCU) | 14–16 SCU | 14–16 SCU | 14–16 SCU | 10–12 SCU | 14–16 SCU | 14–16 SCU |
| Milligrams of Calcium | 334 mg | 334 mg | 334 mg | 250 mg | 300 mg | 300 mg |

*Particle size of about 1 to about 30 microns.
**Used for granulating - not part of final product.

TABLE II

*MICRONIZED CALICUM CITRATE

| | 13 | 14 | 15 | 16 | 17 | 18 |
|---|---|---|---|---|---|---|
| Calcium Citrate Tetrahydrate (micronized) | 71.2% | 71.2% | 71.2% | 71.2% | 71.2% | 71.2% |
| Sugar (6X) | 12.0% | 12.8% | — | — | — | — |
| Mannitol | — | — | — | — | 26.85% | 10.5% |
| Sugar (Fine) | 15.0% | 15.0% | — | — | — | — |
| Cyclamate | 0.6% | — | 1.0% | 1.0% | 1.0% | 2.0% |
| Citric Acid | 0.5% | 0.25% | 0.2% | 0.25% | 0.25% | 0.5% |
| Saccharin | — | 0.10% | — | — | — | — |
| Maltrin M-100 | — | — | — | 2.0% | — | — |
| Polyol Crystals | — | — | — | — | — | — |
| Sorbitol Powder | — | — | 14.6% | 12.9% | — | — |
| Sorbitol Solution (70%) | — | — | 17.1% | 17.1% | — | 21.5% |
| Flavor | 0.17% | 0.17% | 0.5% | 0.2% | 0.2% | 0.3% |
| Magnesium Stearate | 0.5% | 0.5% | 0.5% | 0.5% | 0.5 % | 0.5% |
| **Water (Potable) | 40% | 40% | 20% | 20% | 56% | 29% |
| Tablet Weight | 2.0 g | 2.0 g | 2.0 g | 2.0 g | 2.0 g | 2.0 g |
| Tablet (SCU) Harness | 10–12 SCU | 10–12 SCU | 13–17 SCU | 13–15 SCU | Not Compressed | 13–15 SCU |
| Milligrams of Calcium | 300 mg | 300 mg | 300 mg | 300 mg | 300 mg | 300 mg |

| | 19 | 20 | 21 |
|---|---|---|---|
| Calcium Citrate Tetrahydrate (micronized) | 71.2% | 56.96% | 56.96% |
| Sugar (6X) | — | 26.64% | 16.54% |
| Mannitol | 10.5% | — | — |
| Sugar (Fine) | — | 15.0% | 15.0% |
| Cyclamate | 2.0% | 0.3% | 0.5% |
| Citric Acid | 0.5% | 0.25% | 0.25% |
| Saccharin | — | — | — |
| Polyol Crystals | — | — | — |
| Sorbitol Powder | — | — | — |
| Sorbitol Solution (70%) | 21.5% | — | — |
| Flavor | 0.3% | 0.3% | 0.25% |
| Magnesium Stearate | 0.5% | 0.5% | 0.5% |
| **Water (Potable) | 29% | 25% | 21% |
| Tablet Weight | 2.0 g | 2.5 g | 2.5 g |
| Tablet (SCU) Harness | 13–15 SCU | 14–16 SCU | 12–14 SCU |
| Milligrams of Calcium | 300 mg | 300 mg | 300 mg |

*Particle size of about 0.1 to about 5 microns.
**Used for granulating - not part of final product.

EXAMPLES

Compositions 1-12 represent milled, non-micronized calcium citrate formulations. The particle size of the commercially available calcium citrate crystals used, after milling was about 1 to about 30 micrometers. Although numerous modifications were made to the formulations to make the final tablets palatable and smooth-tasting, this desired result was not achieved due to the strong gritty texture and bitter taste imparted by the calcium crystals. Attempts to mask this unpleasantness with sweeteners and flavors were not effective.

Compositions 13-21 are representative of inventive formulations containing micronized calcium citrate having an average spherical particle size of about 0.94 micronmeters. Tablets formed via standard wet granulation techniques using these formulations were non-gritty and smooth-textured without any bitterness. These tablets exhibited a soft, chewable consistency which exhibited pleasant organoleptic characteristics without the strong chalkiness commonly associated with calcium tablets.

Thus, while these examples described herein are presently believed to be the preferred embodiments of the present invention, it will be appreciated by those skilled in the art that other and further embodiments are contemplated as being with the true scope of the invention and that such changes and modifications are intended to be covered by the present claims.

We claim:

1. A non-gritty, chewable, calcium tablet comprising a granulation having a bulk density of about 0.3 g/ml to about 1.5 g/ml, and 300 mg. of calcium said granulation comprising micronized calcium citrate having a particle size from about 0.1 micronmeters to about 10.0 micronmeters, a sweetener and a lubricant.

2. The tablet of claim 1 wherein the granulation bulk density is about 0.5 to about 1.0 g/ml.

3. The tablet of claim 1 wherein the calcium citrate has a particle size of from about 0.1 to about 5 micronmeters.

4. The tablet of claim 1 wherein the calcium citrate has a particle size of from about 0.1 to about 3 micronmeters.

5. The tablet of claim 1 wherein the sweetener is selected from the group of sucrose, chlorinated sucrose derivatives, glucose, mannose, galactose, saccharin and its salts, cyclamates, acesulfame and its salts, talin, dihydrochalcone, monellin, dipeptide sweeteners, amino acid-based sweeteners, polyols and mixtures therein.

6. The table of claim 1 wherein the lubricant is a stearate.

7. The tablet of claim 1 comprising:
   (1) a granulation bulk density of about 0.5 to about 1.0 g/ml.
   (2) A calcium citrate particle size of about 0.1 to about 3 micronmeters.
   (3) About 10 to about 60% by weight sweetener.
   (4) A lubricant present in sufficient quantity to provide compressibility lubrication.

8. The tablet of claim 1 wherein the calcium citrate is present in amounts of about 25% to about 90% by weight.

9. A non-gritty, compressible granulation having a bulk density of about 0.5 g/ml to about 1.0 g/ml said granulation comprising micronized calcium citrate having a particle size from about 0.1 micronmeters to about 5.0 micronmeters, a sweetener and a lubricant.

10. The granulation of claim 9 wherein the calcium citrate is present in amounts of about 25% to about 90% by weight.

11. The granulation of claim 9 wherein the sweetener is a bulk sweetener present in amounts of about 10% to about 60% by weight.

12. The granulation of claim 9 wherein the lubricant is present in amounts of about 0.1% to about 2% by weight.

13. The granulation of claim 9 wherein the sweetener is selected from the group consisting of sucrose, glucose, mannose, galactose, saccharin and its salts, cyclamates, acesulfame and its salts, talin, monellin, dihydrochalcone, dipeptide sweeteners, amino acid-based sweeteners, polyols, chlorinated sucrose derivatives and mixtures thereof.

14. The granulation of claim 9 wherein the lubricant is selected from the group consisting of stearates, talc, sodium lauryl sulfate, polyethylene glycols, natural waxes, synthetic waxes, sodium acetate, sodium benzoate, sodium oleate and mixtures thereof.

15. The granulation of claim 14 wherein the lubricant is magnesium stearate.

* * * * *

UNITED STATES PATENT AND TRADEMARK OFFICE
CERTIFICATE OF CORRECTION

PATENT NO. : 4,882,161
DATED : November 21, 1989
INVENTOR(S) : Scheurer, et al.

It is certified that error appears in the above-identified patent and that said Letters Patent is hereby corrected as shown below:

In the Abstract, item [57] lines 5 and 6, "micronmeters" should read --micrometers--.

In Column 1, line 51, "0.3/ml" should read --0.3g/ml--.

In Column 1, lines 54 and 68, "micronmeters" should read --micrometers--.

In Column 2, lines 27, 33, and 34 "micronmeters" should read --micrometers--. Line 48, "micromized" should read --micronized--.

In Column 2, line 41, "chew" should read --chewing--.

In Column 4, line 22, "75°" should read --75°C.--.

In Column 4, Table 1, in column 6 of table, "7.12%" should read --71.2%--.

In Column 4, Table 1, line 20, "Harness" should read --Hardness--.

UNITED STATES PATENT AND TRADEMARK OFFICE
CERTIFICATE OF CORRECTION

PATENT NO. : 4,882,161
DATED : November 21, 1989
INVENTOR(S) : Scheurer, et al.

It is certified that error appears in the above-identified patent and that said Letters Patent is hereby corrected as shown below:

In Column 5, Table 1-continued, line 8, "Harness" should read --Hardness--.

In Column 5, Table II, lines 19 and 41, "Harness" should read --Hardness--.

In Column 5, line 67, insert --citrate-- after the word "calcium".

In Column 6, line 60, replace "micronmeters" with --micrometers--.

In Claim 1, lines 5 and 6 thereof, "micronmeters" should read --micrometers--.

In Claim 3, line 2 thereof, "micronm-" should read --microm--.

In Claim 4, line 2 thereof, "micronm-" should read --microm--.

UNITED STATES PATENT AND TRADEMARK OFFICE
CERTIFICATE OF CORRECTION

PATENT NO. : 4,882,161

DATED : November 21, 1989

INVENTOR(S) : Scheurer, et al.

It is certified that error appears in the above-identified patent and that said Letters Patent is hereby corrected as shown below:

In Claim 7, line 5 thereof, "micronmeters" should read --micrometers--.

In Claim 9, lines 4 and 5 thereof, "micronmeters" should read --micrometers--.

Signed and Sealed this

Thirtieth Day of April, 1991

Attest:

HARRY F. MANBECK, JR.

Attesting Officer

Commissioner of Patents and Trademarks